US007102058B2

(12) United States Patent
Cahoon et al.

(10) Patent No.: US 7,102,058 B2
(45) Date of Patent: Sep. 5, 2006

(54) PHYTIC ACID BIOSYNTHETIC ENZYMES

(75) Inventors: Rebecca E. Cahoon, Webster Groves, MO (US); Scott V. Tingey, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 387 days.

(21) Appl. No.: 10/629,950

(22) Filed: Jul. 20, 2003

(65) Prior Publication Data
US 2004/0219561 A1 Nov. 4, 2004

Related U.S. Application Data

(60) Division of application No. 09/686,522, filed on Oct. 11, 2000, now abandoned, which is a continuation of application No. PCT/US99/08791, filed on Apr. 22, 1999.

(60) Provisional application No. 60/082,960, filed on Apr. 24, 1998.

(51) Int. Cl.
*A01H 1/00* (2006.01)
*C07H 21/04* (2006.01)
*C07K 14/415* (2006.01)
*C12N 5/14* (2006.01)
*C12N 9/00* (2006.01)

(52) U.S. Cl. .................. 800/295; 435/6; 435/69.1; 435/468; 435/419; 435/252.3; 435/320.1; 435/183; 530/370; 536/23.6; 800/278

(58) Field of Classification Search .............. 435/6, 435/69.1, 468, 419, 252.3, 320.1, 183; 530/370; 536/23.6; 800/278, 296
See application file for complete search history.

(56) References Cited

U.S. PATENT DOCUMENTS 6,197,561 B1 * 3/2001 Martino-Catt et al. ...... 800/278

FOREIGN PATENT DOCUMENTS

| WO | 91/14782 | 10/1991 |
| WO | 96/05785 | 2/1998 |
| WO | 99/05298 | 2/1999 |
| WO | 99/07211 | 2/1999 |

OTHER PUBLICATIONS

EMBL Sequence Library Data Accession No: D47093, Mar. 9, 1995, Sasaki, T. et al., Rice cDNA from shoot.
EMBL Sequence Library Data Accession No: C72860, Sep. 19, 1997, Sasaki, T. et al., Rice cDNA from panicle at flowering stage.
Monita P. Wilson et al., Biochem. & biophys. Res. Comm.,, vol. 232:678-681, 1997, Characterization of a cDNA encoding arabidopsis thaliana Inositol 1,3,4-trisphosphate 5/6-kinase.
Jia Li et al., Plant Phys., vol. 114:1103-1111, 1997, Secretion of Active Recombinant Phytase from Soybean Cell-Suspensioin Cultures.
Francisco J. Quintero et al., Plant cell, vol. 8:529-537, 1996, The SAL1 Gene of arabidopsis, encoding an Enzyme with 3'(2'),5'-Bisophosphate nucleotidease and Inositol Polyphosphate 1-Phosphatase Activities, Increases salt tolerance in yeast.
Akio Matsuhisa et al., Journ. of Bacteriology, vol. 177(1):200-205, 1995, Inositol Monophosphatase Activity from the *Escherichia coli* suhB gene product.
Gillaspy, Glenda, Plant Phys., vol. 114(3) suppl:314, 1997, Transgenic reduction of inositol monophosphatase disrupts vegetative development, XP-002112476.
Glenda E. Gillaspy et al., Plant Cell, vol. 7:2175-2185, 1995, Plant Inositol Monophosphatase is a Lithium-Sensitive Enzyme Encoded by a Multigene Family.
Barbara, F. Harland et al., J. Assoc. Off. Anal. Chem., vol. 69(4):667-670, 1986, Anion-Exchange Method for Determination of Phytate in Foods: Collaborative Study.
Jean-Claude Pernollet, Phytochemistry, vol. 17:1473-1480, 1978, Protein Bodies of Seeds: Ultrastructure, Biochemistry, Biosynthesis and Degradation.
Boyd L. O'Dell et al., J. Agr. Food Chem., vol. 20(3):718-721, 1972, Distribution of Phytate and Nutritionally Important Elements among the Morphological Components of Cereal Grains.
Z. Mroz et al., J. Animal Science, vol. 72:126-132, 1994, Apparent Digestibility and Retention of Nutrients Bound to Phytate Complexes as Influenced by Microbial Phytase and Feeding Regimen in Pigs.
M. R. Spivey Fox et al., In Nutritional Toxicology, vol. 3, Academic Press, San Diego (1989) pp. 59-96, Antinutritive Effects of Phytate and Other Phosphorylated Derivatives.
Victor Raboy, Inositiol Metabolism in Plants, (1990) Wiley-Liss, New York, pp. 55-76, Biochemistry and Genetics of Phytic Acid Synthesis.
Jan Pen et al., Bio/Technology, vol. 11, Jul. 1993, 811-814, Phytase-containing Transgenic Seeds as a Novel Feed Additive for Improved Phosphorus Utilization.
National Center for Biotechnology Information Generla Identifier No. 1709203, Oct. 1, 2000, Gillaspy, G. E. et al., Plant Inositiol Monophosphatase is a Lithium-sensititive Enzyme Encoded by a Multigene Family.

(Continued)

*Primary Examiner*—Phuong T. Bui

(57) ABSTRACT

This invention relates to an isolated nucleic acid fragment encoding a phytic acid biosynthetic enzyme. The invention also relates to the construction of a chimeric gene encoding all or a portion of the phytic acid biosynthetic enzyme, in sense or antisense orientation, wherein expression of the chimeric gene results in production of altered levels of the phytic acid biosynthetic enzyme in a transformed host cell.

11 Claims, 3 Drawing Sheets

OTHER PUBLICATIONS

Glenda E. Gillaspy et al., The Plant Cell, vol. 7:2175-2185, Dec. 1995, Plant Inositiol Monophosphatase is a Lithium-sensititive Enzyme Encoded by a Multigene Family.

National Center for Biotechnology Information General Identifier No. 1709205, Oct. 1, 2000, Gillaspy, G.E. et al., Plant Inositiol Monophosphatase is a Lithium-sensititive Enzyme Encoded by a Multigene Family.

National Center for Biotechnology Information General Identifier No. 3915048, Dec. 15, 1998, Kaneko, T. et al., Sequence Analysis of the Genome of the Unicellular Cyanobacterium Synechocystis sp. strain PCC6803. Sequence Determination of the Entire Genome and Assignment of Potential Protein-Coding Regions.

Takakazu Kaneko et al., DNA Res., vol. 3:109-136, 1996, Sequence Analysis of the Genome of the Unicellular Cyanobacterium Synechocystis sp. Strain PCC6803. II. Sequence Determination of the Entire Genome and Assignment of Potential Protein-coding Regions.

National Center for Biotechnology Information General Identifier No. 1652942, Feb. 7, 1999, Kaneko, T. et al., Sequence Analysis of the Genome of the Unicellular Cyanobacterium Synechocystis sp. Strain PCC6803. II. Sequence Determination of the Entire Genome and Assignment of Potential Protein-coding Regions.

\* cited by examiner

Figure 1

```
                                1                                                              60
SEQ ID NO:21 (gi 1709203)       MARNGSLEEFLGVAVDAAKRAGEIIRKGFHETKHVHKGQVDLVTETDKACEDLIFNHLK
SEQ ID NO:22 (gi 1709205)       MAQNGSVEQFLDVAVEAAKKAGEIIREGFYKTKHVEHKGMVDLVTETDKACEDFIFNHLK
SEQ ID NO:2                     MAE---EQFLAVAVDAAKNAGEIIRKGFYQTKNVEHKGQVDLVTETDKACEDLIFNHLR
SEQ ID NO:4                     MVDNDSLSEFLASAVDAAQKAGEIIRKGFYQTKNVEHKGQVDLVTETDKACEELIFNHLK
SEQ ID NO:6
SEQ ID NO:8                     MAE----EQFLAAAVGAAKSAGEIIRKSFYLSKKVEHKGQVDLVTETDKACEDLIFNHLR 61                                                             120
SEQ ID NO:21 (gi 1709203)       QHFPSHKFIGEETSAAT-GDFDLTDEPTWIVDPVDGTTNFVHGFPSVCVSIGLTIGKIPT
SEQ ID NO:22 (gi 1709205)       QRFPPSHKFIGEETTAA-CGNFELTDEPTWIVDPLDGTTNFVHGFPFVCVSIGLTIEKKPT
SEQ ID NO:2                     KHYPDHKFIGEETSAGLGATADLTDDPTWIVDPLDGTTNFVHGFPFVCVSIGLTVGK---
SEQ ID NO:4                     QLYPTHKFIGEETTAA-YGTTELTDEPTWIVDPLDGTTNFVHGFPFVCVSIGLTIGKTPT
SEQ ID NO:6
SEQ ID NO:8                     MLYPDIHKFIGEETSAALGSTDDLTYDPTWIVDPLDGTTNFVHGFPFVCVSIGLTIGKIPT 121                                                            180
SEQ ID NO:21 (gi 1709203)       VGVVYDPIIDELFTGINGKGAYLNGKPIKVSSQSELVKSLLGTEVGTTRDNLTVETTTRR
SEQ ID NO:22 (gi 1709205)       VGVVYNPIIDELFTGIDGKGAFLNGKPIKVSSQSELVKALLATEAGTNRDKLVDATTGR
SEQ ID NO:2                     IGVVYNPIINELFTGIHGKGAFLNGNPIKVSSQTELISSLLATEAGTKR---
SEQ ID NO:4                     VGVVYNPIMNELFTAVRGKGAFLNGSPIKTSPQNELVKALMVTEVGTKRDKSTLDDTTNR
SEQ ID NO:6
SEQ ID NO:8

181                                                            240
SEQ ID NO:21 (gi 1709203)       INNLLFKVRSLRMCGSCALDLCWVACGRLELFYLIGYGGPWDVAGGAVIVKEAGGVLFDP
SEQ ID NO:22 (gi 1709205)       INSLLFKVRSLRMCGSCALNLCGVACGRLDLFYELEFGGPWDVAGGAVIVKEAGGFVFDP
SEQ ID NO:2                     ----------------------------------------VLRGGAGLS---
SEQ ID NO:4                     ------IACGRLDVFFELGFGGPWDVAGGAVIVREAGGVVFDP
SEQ ID NO:6
SEQ ID NO:8                     INKLLFKIRSIRMCGSLALNMCGVACGRLDLCYEIGFGGPWDVAAGALILKEAGGFVFDP 241                                      277
SEQ ID NO:21 (gi 1709203)       SGSEFDITSQRVAATNPHLKEAFVEA---LQLSEYVS
SEQ ID NO:22 (gi 1709205)       SGSEFDLTARRVAATNAHLKDAFIKA---LNE------
SEQ ID NO:2                                                    ------I
SEQ ID NO:4                                                    ------T
SEQ ID NO:6                     SGADFAITSQRVAVSNPFXKDELVETRRKMGWEIYN.
SEQ ID NO:8                     SGDEFDLMAQRMAGSNGHLKDQFIKA--LGDAS.--
```

Figure 2A

```
                         1                                                              60
SEQ ID NO:23 (gi 3915048) M----TSAQKPVF-------------------SPSDLQT----------------WL--
SEQ ID NO:24 (gi 1652942) ML--------------------------PEVEQRLF------------------------
SEQ ID NO:10              ------------------------------------------------------------
SEQ ID NO:12              MLSSSSSTHSDTSPFPGLASANPNPRSRLLRLRAASPVSSAVLSASGRQP------MSTV
SEQ ID NO:14              ------------------------------------------------------------
SEQ ID NO:16              MFSQCH--------FLSHSPIPNTT-FRLRAMAPHST-----------------------
SEQ ID NO:18              ---------HETKPSLP-------------------------------------------
SEQ ID NO:20              ----------------------YHLRSPSLLATFSSSAAGRACGIAGRWMGSV 61                                                            120
SEQ ID NO:23 (gi 3915048) -------------------EIATEAVLAAGAEI--FSLWGKVQQIQEKGRAG
SEQ ID NO:24 (gi 1652942) -------------------IAQQLAAVSGEILIQYFRRSHLQGGTKIDQVS
SEQ ID NO:10              ------------------------------------------------------------
SEQ ID NO:12              RASFAAGAAGRRAAAVGE--LATERLVEVAQRAADAAGEVLRKYFRQ-RVEIIDKEDHSP
SEQ ID NO:14              ------------------------------------------------------------
SEQ ID NO:16              -------------------PLELNRFAEVGNKVADAAGEVIRKYFRK-NFDVIHKHDLSP
SEQ ID NO:18              ------------------------------------------------------------
SEQ ID NO:20              RAS-PSEAGGWAVAAAGKEGVDMERLVAVAQSAADAAGEVLRKYFRQ-RFEIIDKEDHSP 121                                                            180
SEQ ID NO:23 (gi 3915048) DLVTEADRQAEAIILEIIKRRCPDHAILAEESG-QLGQVDNPFCWAIDPLDGTTNFAHSY
SEQ ID NO:24 (gi 1652942) AIVTQADEEAEQAMVDLIQAQFPQDGVIREEG--KNIAGKSGYTWVLDPIDGTSSFVRGL
SEQ ID NO:10              ----HEDKLSESVILEVVTKNFRDHLILGEEGG-LIGDSLSEYLWCIDPLDGTTNFAHGY
SEQ ID NO:12              --VTIADREAEEAMVSVILKSFPTHAIFGEENGWRCAENSADFVWVLDPIDGTKSFITGK
SEQ ID NO:14              ----HE------------------------------------------------------
SEQ ID NO:16              --VTIADQSAEEAMVSIILDNFPSHAIYGEENGWRCEEKNADYVWVLDPIDGTKSFITGK
SEQ ID NO:18              --VTIADREAEEAMTSVILKSFPTHAVFGEENGWRCAEKSADYVWVLDPIDGTKSFITGK
SEQ ID NO:20              ------------------------------------------------------------
```

Figure 2B

```
                              181                                                        240
SEQ ID NO:23 (gi 3915048)     PVSCVSIGLLIQDIPTVGVVYNPFRQELFRAATSLGATLNR-----RPIQVSTTASLDK
SEQ ID NO:24 (gi 1652942)     PIFATLIGLVDADMRPVLGIAHQPISGDRWQGVQGEQSNVNGIP-LVNPYKASEINLTAA
SEQ ID NO:10                  PSFSVSIGVLYRGKPAAATVVEFCGGPMCWSTRTISASSGKGAYCNGQKIHVSPTEKVEQ
SEQ ID NO:12                  -----------------MCWTTRTIFPFAGGGAYYIGQRIHVSQTDKVEQ
SEQ ID NO:14                  PLFGTLIALLHNG-KPVIGVIDQPILRERWIGVDGKQTTLNGQE-I--SVRSCNL-LAQA
SEQ ID NO:16                  ----------------------------------------------LTKVEQ
SEQ ID NO:18                  PVFGTLVALLQNG-TPILGIIDQPVLRERWIGIAGKRTSLNGQE-I--STRTCAD-LSQA
SEQ ID NO:20                  PLFGTLIALLHNG-KPVMGIIDQPILRERWVGVDGKKTTLNGQE-I--SVRPCNV-LEQA 241                                                        300
SEQ ID NO:23 (gi 3915048)     SLLVTG---FAYDRVKTLDNNYPEFCYLTHLTQGVRRSGSAAIDLIDVACGRLDGYWERG
SEQ ID NO:24 (gi 1652942)     CIVSTTPLMFTTPVQQQKMADIYRQCQRTAFGGDCFNYLSAASGWTAMPLVIVEA----D
SEQ ID NO:10                  SLLVTG---FGYEHDDAWLTNINLFKEFTDVSRGVRRLGSAAADMSHVGLGITEAYWEYR
SEQ ID NO:12                  SLLVTGFGYEHDDAWTTNMNLFKEFTDISRGVRR--LGSACYALLASGFVDI---VVES------G
SEQ ID NO:14                  YLYTTSPHLFEADAEDA-FIRVRNKVKVPLYGCDCYAYALLASGFVDI---VVES------G
SEQ ID NO:16                  SLLVTG---FGYEHDDAWVTNINLFKEYTDISRGVRRLGSAAADMSHVALGITEAYWEYR
SEQ ID NO:18                  YLYTTSPHLFNGDAEEA-FIRVSKVKFQLYGCDCYAYALLSSGFVDL---VVES------G
SEQ ID NO:20                  YLYTTSPHLFEGDAEDA-FIRVRDKVKVPLYGCDCYAYALLASGFVDL---VVES------G 301                                                        360
SEQ ID NO:23 (gi 3915048)     INPWDMAAGIVIVREAGGIVSAYDCSPLDLSTGRILATNGKIHQELSQALAATPQ----
SEQ ID NO:24 (gi 1652942)     LNFYDFCALIPILTGANYCFTDWQGKEL----------TPESTEVVASPNPKLHSE
SEQ ID NO:10                  LKPWDMAAGVLIVEEAGGVVTRMDGGEFTVFDRSVLVSNGVVHDQLLERIRPATEDLKKK
SEQ ID NO:12                  YRLKPWDVHAGVLIVEEAGGVVTRMDGGEFTVFDRSVLVSNGLVHGQV----
SEQ ID NO:14                  LKPWDFLSLVPVIEGAGGSITDWRGDKLH-----WPVTAESRPTSFNVVAAGDARVHKE
SEQ ID NO:16                  LKPWDMAAGVLIVEEAGGMVSRMDGGEFTVFDRSVLVSNGVVHDQLLDRIGPATEDLKKK
SEQ ID NO:18                  LKPYDFLALIPVIEGAGGVITDWKGDKLF------WEASPLSIATSFNVVAAGDKQIHQQ
SEQ ID NO:20                  LKPYDFLSLVPVIEGAGGSITDWEGNKLH------WPVSSESRPTSFNVVAAGDSHVHGQ 361      381
SEQ ID NO:23 (gi 3915048)     ILAFL---Q-------
SEQ ID NO:24 (gi 1652942)     ------WF--QQYAAARAQKI
SEQ ID NO:10                  GIDFSLWFKPDKYPT---DF.
SEQ ID NO:12                  ---------------CL
SEQ ID NO:14                  ALDALRWR.-------
SEQ ID NO:16                  GIDFSLWFKPDKYPT---DF.
SEQ ID NO:18                  ALDSLQWK.-------
SEQ ID NO:20                  ALAALRWR.-------
```

PHYTIC ACID BIOSYNTHETIC ENZYMES

This application is a divisional of U.S. application Ser. No. 09/686,522, filed Oct. 11, 2000, now abandoned which is a continuation of International Application No. PCT/US99/08791, filed Apr. 22, 1999, which claims the benefit of U.S. Provisional Application No. 60/082,960, filed Apr. 24, 1998.

FIELD OF THE INVENTION

This invention is in the field of plant molecular biology. More specifically, this invention pertains to nucleic acid fragments encoding phytic acid biosynthetic enzymes in plants and seeds.

BACKGROUND OF THE INVENTION

Myo-inositol 1,2,3,4,5,6-hexaphosphate, commonly known as phytic acid, is an abundant molecule in many plant seeds and vegetative tissue such as roots and tubers (Hartland and Oberlaeas (1986) *J. Assoc. Off. Anal. Chem.* 69:667–670). Phytic acid exists primarily as mixture of potassium, calcium, iron, zinc and magnesium phytate salts (Pernollet J. C. (1978) *Phytochemistry* 17:1473–1480).

In corn (*Zea mays L.*), 90% of the phytate is deposited in protein bodies localized in the germ whereas in legume crops 90% of the phytate is localized in the endosperm and cotyledons. Up to 80% of phytate is in the aluerone layer of wheat (*Triticum aestivum Lam.*) and rice (*Oryza sative L.*) (O'Dell B. L. et al. (1972) *J. Agric. Food Chem.* 20:718–721). The presence of phytate phosphorous in such food crops decreases the bioavailability of zinc by forming a very stable insoluble phytate zink complex, making the zinc unavailable in the intestinal mucosa of mammals (O'Dell, B. L., et al. (1972) *J. Agr. Food Chem.* 20:718–721). Although phytate phosphorous is readily available to ruminants, it is poorly available to monogastric animals. In addition to being only partially digestible, the presence of phytic acid in food crops leads to excretion of other limiting nutrients such as essential amino acids, calcium and zinc (Mroz, Z. et al. (1994) *J. Animal Sci.* 72:126–132; Fox et al., In Nutritional Toxicology Vol. 3, Academic Press, San Diego (1989) pp. 59–96).

Phytic acid is thought to arise in plants by two pathways. The first pathway uses free myo-inositol as the initial substrate, with subsequent phosphorylation by a phosphoinositol kinase. Contribution to the free myo-inositol pool is either by recycling from other pathways or by the dephosphorylation of myo-inositol-1-phosphate. The alternate pathway uses myo-inositol-1-phosphate as the initial substrate, with subsequent phosphorylations catalyzed by phosphoinositol kinase. The committed step for myo-inositol-1-phosphate production is the $NAD^+$-catalyzed oxidation of carbon 5 of the b-enantiomer of D-glucose-6-phosphate. This reaction is catalyzed by myo-inositol-1-phosphate synthase (Raboy, V. In Inositol Metabolism in Plants (1990) Wiley-Liss, New York, pp. 55–76).

Phytic acid is degraded in plant cells to D-myo-inositol 1,2,4,5,6-pentakisphosphate and orthophosphate through the action of phytase. Manipulation of this enzyme activity could lead to a reduction of phytic acid levels in seeds and an increase in inositol trisphosphate and free phosphate, thus making phosphorus more metabolically available to animals that are fed the seed. Another method to lower phytic acid levels is by inhibiting the activity of myo-inositol-1 (or 4)-monophosphatase, which catalyzes the reaction: myo-inositol 1-phosphate+$H_2O$=myo-inositol+orthophosphate. Manipulation of the activity of this enzyme in developing seeds could decrease phytic acid levels in seeds and increase levels of free phosphate. Lastly, phytic acid levels could also be reduced by inhibiting the activity of inositol trisphosphate kinase. This enzyme catalyzes the reaction: ATP+1D-myo-inositol 1,3,4-trisphosphate=ADP+1D-myo-inositol 1,3,4,6-tetrakisphosphate. This reaction is one of the final steps leading to the formation of Myo-Inositol 1,2,3,4,5,6-hexaphosphate (phytic acid). Reduction in the activity of the enzyme in developing seeds would interrupt phytic acid synthesis leaving the phosphate as the more metabolically available inositol trisphosphate and free phosphate.

In the United States, corn accounts for about 80% of the grain fed to all classes of livestock, including poultry, and is usually ground before feeding (Corn: Chemistry and Technology, 1987, American Association of Cereal Chemists, Inc., Edited by Stanley A. Watson and Paul E. Ramstad). A meal with decreased amounts of phytic acid and increased amounts of available phosphate would lead to improved feed efficiency in corn-containing rations, making available certain minerals especially zinc, magnesium, iron and calcium. Indeed, enzymatic treatment of soybean meal-containing rations to partially hydrolyze the phosphate groups from phytic acid improves both phosphate availability and the availability of other limiting nutrients. Also, in the wet milling of corn, phytate in the steepwater tends to precipitate, causing problems in handling, storing and transportation of the steep liquor. (Pen et al. (1993) *Biotechnology* 11:811–814). In light of these factors, it is apparent that corn plants with heritable, substantially reduced levels of phytic acid and increased levels of free phosphorous in their seeds would be desirable. Accordingly, the availability of nucleic acid sequences encoding all or a portion of these enzymes would facilitate studies to better understand carbohydrate metabolism and function in plants, provide genetic tools for the manipulation of these biosynthetic pathways, and provide a means to control carbohydrate transport and distribution in plant cells.

SUMMARY OF THE INVENTION

The instant invention relates to isolated nucleic acid fragments encoding phytic acid biosynthetic enzymes. Specifically, this invention concerns an isolated nucleic acid fragment encoding a myo-inositol-1 (or 4)-monophosphatase or a plant homolog of the *Synechocystis* sp. extragenic suppressor protein, a protein in the inositol monophosphatase family of proteins (Keneko, T., et al., (1996) *DNA Res.* 3(3):109–136). In addition, this invention relates to a nucleic acid fragment that is complementary to the nucleic acid fragment encoding a myo-inositol-1 (or 4)-monophosphatase or extragenic suppressor protein.

An additional embodiment of the instant invention pertains to a polypeptide encoding all or a substantial portion of a phytic acid biosynthetic enzyme selected from the group consisting of myo-inositol-1 (or 4)-monophosphatase and extragenic suppressor proteins.

In another embodiment, the instant invention relates to a chimeric gene encoding a myo-inositol-1 (or 4)-monophosphatase or extragenic suppressor protein, or to a chimeric gene that comprises a nucleic acid fragment that is complementary to a nucleic acid fragment encoding a myo-inositol-1 (or 4)-monophosphatase or extragenic suppressor protein, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a myo-inositol-1 (or 4)-monophos-phatase or extragenic suppressor protein, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a myo-inositol-1 (or 4)-monophosphatase or extragenic suppressor protein in a transformed host cell comprising: a) transforming a host cell with a chimeric gene comprising a nucleic acid fragment encoding a myo-inositol-1 (or 4)-monophosphatase or extragenic suppressor protein; and b) growing the transformed host cell under conditions that are suitable for expression of the chimeric gene wherein expression of the chimeric gene results in production of altered levels of myo-inositol-1 (or 4)-monophosphatase or extragenic suppressor protein in the transformed host cell.

An addition embodiment of the instant invention concerns a method for obtaining a nucleic acid fragment encoding all or a substantial portion of an amino acid sequence encoding a myo-inositol-1 (or 4)-monophosphatase or extragenic suppressor protein.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIG. 1 presents an alignment of the amino acid sequence set forth in SEQ ID NOs:2, 4, 6 and 8 with the *Lycopersicon esculentum* IMP amino acid sequences (SEQ ID NO:21 and 22). Alignments were performed using the Clustal algorithm.

FIGS. 2A and 2B present an alignment of the amino acid sequence set forth in SEQ ID NOs:10, 12, 14, 16, 18 and 20 with the *Synechocystis* sp. extragenic suppressor protein amino acid sequences (SEQ ID NO:23 and 24). Alignments were performed using the Clustal algorithm.

The following sequence descriptions and Sequence Listing attached hereto comply with the rules governing nucleotide and/or amino acid sequence disclosures in patent applications as set forth in 37 C.F.R. §1.821–1.825.

SEQ ID NO:1 is the nucleotide sequence comprising a portion of the cDNA insert in clone r10n.pk127.f22 encoding a portion of a rice myo-inositol-1 (or 4)-monophosphatase.

SEQ ID NO:2 is the deduced amino acid sequence of a portion of a myo-inositol-1 (or 4)-monophosphatase derived from the nucleotide sequence of SEQ ID NO:1.

SEQ ID NO:3 is the nucleotide sequence comprising a portion of the cDNA insert in clone sfl1.pk0034.a12(5') encoding a portion of a soybean myo-inositol-1 (or 4)-mono-phosphatase.

SEQ ID NO:4 is the deduced amino acid sequence of a portion of a myo-inositol-1 (or 4)-monophosphatase derived from the nucleotide sequence of SEQ ID NO:3.

SEQ ID NO:5 is the nucleotide sequence comprising a portion of the cDNA insert in clone sfl1.pk0034.a12(3') encoding a portion of a soybean myo-inositol-1 (or 4)-monophosphatase.

SEQ ID NO:6 is the deduced amino acid sequence of a portion of a myo-inositol-1 (or 4)-monophosphatase derived from the nucleotide sequence of SEQ ID NO:5.

SEQ ID NO:7 is the nucleotide sequence comprising a the entire cDNA insert in clone wlmk1.pk0020.a9 encoding a wheat myo-inositol-1 (or 4)-monophosphatase.

SEQ ID NO:8 is the deduced amino acid sequence of a myo-inositol-1 (or 4)-monophosphatase derived from the nucleotide sequence of SEQ ID NO:7.

SEQ ID NO:9 is the nucleotide sequence comprising a portion of the cDNA insert in clone bsh1.pk0007.g11 encoding a portion of a barley extragenic suppressor protein.

SEQ ID NO:10 is the deduced amino acid sequence of a portion of an extragenic suppressor protein derived from the nucleotide sequence of SEQ ID NO:9.

SEQ ID NO:11 is the nucleotide sequence comprising a portion of the cDNA insert in clone cco1n.pk066.p15 encoding a portion of a corn extragenic suppressor protein.

SEQ ID NO:12 is the deduced amino acid sequence of a portion of an extragenic suppressor protein derived from the nucleotide sequence of SEQ ID NO:11.

SEQ ID NO:13 is the nucleotide sequence comprising the entire cDNA insert in clone cdt2c.pk003.b20 encoding a corn extragenic suppressor protein.

SEQ ID NO:14 is the deduced amino acid sequence of a portion of an extragenic suppressor protein derived from the nucleotide sequence of SEQ ID NO:13.

SEQ ID NO:15 is the nucleotide sequence comprising a portion of the cDNA insert in clone r10n.pk0062.c6 encoding a portion of a rice extragenic suppressor protein.

SEQ ID NO:16 is the deduced amino acid sequence of a portion of an extragenic suppressor protein derived from the nucleotide sequence of SEQ ID NO:15.

SEQ ID NO:17 is the nucleotide sequence comprising a contig assembled from portions of the cDNA inserts in clones s12.pk122.p24, src3c.pk013.g15 and sfl1n.pk003.g19 encoding a soybean extragenic suppressor protein.

SEQ ID NO:18 is the deduced amino acid sequence of an extragenic suppressor protein derived from the nucleotide sequence of SEQ ID NO:17.

SEQ ID NO:19 is the nucleotide sequence comprising a portion of the cDNA insert in clone wlm0.pk0010.f6 encoding a portion of a wheat extragenic suppressor protein.

SEQ ID NO:20 is the deduced amino acid sequence of a portion of an extragenic suppressor protein derived from the nucleotide sequence of SEQ ID NO:19.

SEQ ID NO:21 is the amino acid sequence of myo-inositol-1 (or 4)-monophosphatase from *Lycopersicon esculentum* (NCBI Identification No. gi 1709203).

SEQ ID NO:22 is the amino acid sequence of myo-inositol-1 (or 4)-monophosphatase from *Lycopersicon esculentum* (NCBI Identification No. gi 1709205).

SEQ ID NO:23 is the amino acid sequence of extragenic suppressor protein from *Synechocystis* sp. (NCBI Identification No. gi 3915048).

SEQ ID NO:24 is the amino acid sequence of extragenic suppressor protein from *Synechocystis* sp. (NCBI Identification No. gi 1652942).

The Sequence Listing contains the one letter code for nucleotide sequence characters and the three letter codes for amino acids as defined in conformity with the IUPAC-IUBMB standards described in *Nucleic Acids Research*

13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. As used herein, "contig" refers to an assemblage of overlapping nucleic acid sequences to form one contiguous nucleotide sequence. For example, several DNA sequences can be compared and aligned to identify common or overlapping regions. The individual sequences can then be assembled into a single contiguous nucleotide sequence.

As used herein, "substantially similar" refers to nucleic acid fragments wherein changes in one or more nucleotide bases results in substitution of one or more amino acids, but do not affect the functional properties of the protein encoded by the DNA sequence.

"Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products.

Moreover, substantially similar nucleic acid fragments may also be characterized by their ability to hybridize, under stringent conditions (0.1×SSC, 0.1% SDS, 65° C.), with the nucleic acid fragments disclosed herein.

Substantially similar nucleic acid fragments of the instant invention may also be characterized by the percent similarity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% similar to the amino acid sequences reported herein. More preferred nucleic acid fragments encode amino acid sequences that are 90% similar to the amino acid sequences reported herein. Most preferred are nucleic acid fragments that encode amino acid sequences that are 95% similar to the amino acid sequences reported herein. Sequence alignments and percent similarity calculations were performed using the Megalign program of the LASARGENE bioinformatics computing suite (DNASTAR Inc., Madison, Wis.). Multiple alignment of the sequences was performed using the Clustal method of alignment (Higgins, D. G. and Sharp, P. M. (1989) *CABIOS*. 5:151–153) with the default parameters (GAP PENALTY=10, GAP LENGTH PENALTY=10), (hereafter Clustal algorithm). Default parameters for pair-wise alignments using the Clustal method were KTUPLE 1, GAP PENALTY=3, WINDOW=5 and DIAGONALS SAVED=5.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the myo-inositol-1 (or 4)-monophosphatase or extragenic suppressor proteins as set forth in SEQ ID NOs:2, 4, 6, 8, 10, 12, 14, 16, 18 and 20.

The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed MRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms. "Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Maniatis").

Nucleic acid fragments encoding at least a portion of several phytic acid biosynthetic enzymes have been isolated and identified by comparison of random plant cDNA sequences to public databases containing nucleotide and protein sequences using the BLAST algorithms well known to those skilled in the art. Table 1 lists the proteins that are described herein, and the designation of the cDNA clones that comprise the nucleic acid fragments encoding these proteins.

TABLE 1

Phytic Acid Biosynthetic Enzymes

| Enzyme | Clone | Plant |
|---|---|---|
| Myo-inositol-1 | rl0n.pk127.f22 | Rice |
| (or 4)-monophosphatase 1 | sfl1.pk0034.a12(5') | Soybean |
| | sfl1.pk0034.a12(3") | Soybean |
| | wlmk1.pk0020.a9 | wheat |
| Extragenic suppressor | bsh1.pk0007.g11 | Barley |
| protein | cco1n.pk066.p15 | Corn |
| | cdt2c.pk003.b20 | Corn |
| | rl0n.pk0062.c6 | Rice |
| | sl2.pk122.p24 | Soybean |
| | src3c.pk013.g15 | Soybean |
| | sfl1n.pk003.g19 | Soybean |
| | wlm0.pk0010.f6 | Wheat |

The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other myo-inositol-1 (or 4)-monophosphatase or extragenic suppressor proteins, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *PNAS USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS USA* 86:5673; Loh et al., (1989)

*Science* 243:217). Products generated by the 3' and 5' RACE procedures can be combined to generate full-length cDNAs (Frohman, M. A. and Martin, G. R., (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragments of the instant invention may be used to create transgenic plants in which the disclosed myo-inositol-1 (or 4)-monophosphatase or extragenic suppressor proteins are present at higher or lower levels than normal or in cell types or developmental stages in which they are not normally found. This would have the effect of altering the level of phytic acid biosynthesis in those cells.

Overexpression of the myo-inositol-1 (or 4)-monophosphatase or extragenic suppressor proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant phytic acid biosynthetic enzymes to different cellular compartments, or to facilitate its secretion from the cell. It is thus envisioned that the chimeric gene described above may be further supplemented by altering the coding sequence to encode myo-inositol-1 (or 4)-monophosphatase or extragenic suppressor protein with appropriate intracellular targeting sequences such as transit sequences (Keegstra, K. (1989) *Cell* 56:247–253), signal sequences or sequences encoding endoplasmic reticulum localization (Chrispeels, J. J., (1991) *Ann. Rev. Plant Phys. Plant Mol. Biol.* 42:21–53), or nuclear localization signals (Raikhel, N. (1992) *Plant Phys.* 100: 1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding myo-inositol-1 (or 4)-monophosphatase or extragenic suppressor protein in plants for some applications. In order to accomplish this, a chimeric gene designed for co-suppression of the instant phytic acid biosynthetic enzymes can be constructed by linking a gene or gene fragment encoding a myo-inositol-1 (or 4)-monophosphatase or extragenic suppressor protein to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

The instant myo-inositol-1 (or 4)-monophosphatase or extragenic suppressor proteins (or portions thereof) may be produced in heterologous host cells, particularly in the cells of microbial hosts, and can be used to prepare antibodies to the these proteins by methods well known to those skilled in the art. The antibodies are useful for detecting myo-inositol-1 (or 4)-monophosphatase or extragenic suppressor proteins in situ in cells or in vitro in cell extracts. Preferred heterologous host cells for production of the instant myo-inositol-1 (or 4)-monophosphatase or extragenic suppressor proteins are microbial hosts. Microbial expression systems and expression vectors containing regulatory sequences that direct high level expression of foreign proteins are well known to those skilled in the art. Any of these could be used to construct a chimeric gene for production of the instant myo-inositol-1 (or 4)-monophosphatase or extragenic suppressor proteins. This chimeric gene could then be introduced into appropriate microorganisms via transformation to provide high level expression of the encoded phytic acid biosynthetic enzymes. An example of a vector for high level expression of the instant myo-inositol-1 (or 4)-monophosphatase or extragenic suppressor proteins in a bacterial host is provided (Example 7).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) *Am. J Hum. Genet.* 32:314–331).

The production and use of plant gene-derived probes for use in genetic mapping is described in R. Bernatzky, R. and Tanksley, S. D. (1986) *Plant Mol. Biol. Reporter* 4(1): 37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In:*Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask, B. J. (1991) *Trends Genet.* 7:149–154). Although current methods of FISH mapping favor use of large clones (several to several hundred KB; see Laan, M. et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian, H. H. (1989) *J. Lab. Clin. Med.* 114(2):95–96), polymorphism of PCR-amplified fragments (CAPS; Sheffield, V. C. et al. (1993) *Genomics* 16:325–332), allele-specific ligation (Landegren, U. et al. (1988) *Science* 241:1077–1080), nucleotide extension reactions (Sokolov, B. P. (1990) *Nucleic Acid Res.* 18:3671), Radiation Hybrid Mapping (Walter, M. A. et al. (1997) *Nature Genetics* 7:22–28) and Happy Mapping (Dear, P. H. and Cook, P. R. (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer, (1989) *Proc. Natl. Acad. Sci USA* 86:9402; Koes et al., (1995) *Proc. Natl. Acad. Sci USA* 92:8149; Bensen et al., (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the myo-inositol-1 (or 4)-monophosphatase or extragenic suppressor protein. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding a myo-inositol-1 (or 4)-monophosphatase or extragenic suppressor protein can be identified and obtained. This mutant plant can then be used to determine or confirm the natural function of the gene product.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various barley, corn, rice, soybean and wheat tissues were prepared. The characteristics of the libraries are described below.

TABLE 2 cDNA Libraries from Barley, Corn, Rice, Soybean and Wheat

| Library | Tissue | Clone |
| --- | --- | --- |
| bsh1 | Barley sheath, developing seedling | bsh1.pk0007.g11 |
| cco1n | Corn (*Zea mays* L.) cob of 67 day old plants grown in green house* | cco1n.pk066.p15(3') |
| cdt2c | Corn (*Zea mays* L.) developing tassel | cdt2c.pk003.b20 |
| rl0n | Rice (*Oryza sativa* L.) 15 day leaf* | rl0n.pk0062.c6 rl0n.pk127.f22 |
| sfl1 | Soybean (*Glycine max* L.) immature flower | sfl1.pk0034.a12(5') sfl1.pk0034.a12(3") |
| sfl1n | Soybean (*Glycine max* L.) immature flower* | sfl1n.pk003.g19 |
| sl2 | Soybean (*Glycine max* L.) two week old developing seedlings treated with 2.5 ppm chlorimuron | sl2.pk122.p24 |
| src3c | Soybean (*Glycine max* L., Bell) 8 day old root inoculated with eggs of cyst nematode *Heterodera glycines* (Race 14) for 4 days. | src3c.pk013.g15 |
| wlm0 | Wheat (*Triticum aestivum* L.) seedlings 0 hr after inoculation with *Erysiphe graminis* f. sp *tritici* | wlm0.pk0010.f6 |
| wlmk1 | Wheat (*Triticum aestivum* L.) seedlings 1 hr after inoculation with *Erysiphe graminis* f. sp *tritici* and treatment with fungicide** | wlmk1.pk0020.a9 |

*These libraries were normalized essentially as described in U.S. Pat. No. 5,482,845
**Application of 6-iodo-2-propoxy-3-propyl-4(3H)-quinazolinone; synthesis and methods of using this compound are described in USSN 08/545,827, incorporated herein by reference.

cDNA libraries were prepared in Uni-ZAP™ XR vectors according to the manufacturer's protocol (Stratagene Cloning Systems, La Jolla, Calif.). Conversion of the Uni-ZAP™ XR libraries into plasmid libraries was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams, M. D. et al., (1991) *Science* 252:1651). The resulting ESTs were analyzed using a Perkin Elmer Model 377 fluorescent sequencer.

Example 2

Identification of cDNA Clones

ESTs encoding phytic acid biosynthetic enzymes were identified by conducting BLAST (Basic Local Alignment Search Tool; Altschul, S. F., et al., (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272 and Altschul, Stephen F., et al. (1997) *NucleicAcids Res.* 25:3389–3402) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Myo-Inositol-1 (or 4)-Monophosphatase Homologs The BLASTX search using the EST sequences from clones r10n.pk127.f22 and sfl1.pk0034.a12(3') revealed similarity of the proteins encoded by the cDNAs to myo-inositol-1 (or 4)-monophosphatase 1 from *Lycopersicon esculentum*. (NCBI Identification No. gi 1709203). The BLASTX search using the EST sequences from clones sfl1.pk0034.a12(5') and wlmk1.pk0020.a9 revealed similarity of the proteins encoded by the cDNAs to myo-inositol-1 (or 4)-monophosphatase 3 from *Lycopersicon esculentum*. (NCBI Identification No. gi 1709205).

The BLAST results for each of these ESTs are shown in Table 3:

TABLE 3

BLAST Results for Clones Encoding Polypeptides Homologous to *Lycopersicon esculentum* Myo-Inositol-1 (or 4)-Monophosphatase Proteins

| Clone | BLAST pLog Score |
|---|---|
| rl0n.pk127.f22 | 54.40 |
| sfl1.pk0034.a12(5') | 89.00 |
| sfl1.pk0034.a12(3') | 23.70 |
| wlmk1.pk0020.a9 | 130.00 |

The sequence of a portion of the cDNA insert from clone r10n.pk127.f22 is shown in SEQ ID NO:1; the deduced amino acid sequence of this cDNA, which represents 42% of the of the protein (N-terminal region), is shown in SEQ ID NO:2. A calculation of the percent similarity of the amino acid sequence set forth in SEQ ID NO:2 and the *Lycopersicon esculentum* sequence (using the Clustal algorithm) revealed that the protein encoded by SEQ ID NO:2 is 77% similar to the *Lycopersicon esculentum* IMP-1 protein.

The sequence of a portion of the cDNA insert from clone sfl1.pk0034.a12(5') is shown in SEQ ID NO:3; the deduced amino acid sequence of this cDNA, which represents 63% of the of the protein (N-terminal region), is shown in SEQ ID NO:4. A calculation of the percent similarity of the amino acid sequence set forth in SEQ ID NO:4 and the *Lycopersicon esculentum* sequence (using the Clustal algorithm) revealed that the protein encoded by SEQ ID NO:4 is 74% similar to the *Lycopersicon esculentum* IMP-3 protein.

The sequence of a portion of the cDNA insert from clone sfl1.pk0034.a12(3') is shown in SEQ ID NO:5; the deduced amino acid sequence of this cDNA, which represents 27% of the of the protein (C-terminal region), is shown in SEQ ID NO:6. A calculation of the percent similarity of the amino acid sequence set forth in SEQ ID NO:6 and the *Lycopersicon esculentum* sequence (using the Clustal algorithm) revealed that the protein encoded by SEQ ID NO:6 is 58% similar to the *Lycopersicon esculentum* IMP-1 protein.

The sequence of the entire cDNA insert from clone wlmk1.pk0020.a9 is shown in SEQ ID NO:7; the deduced amino acid sequence of this cDNA, which represents 100% of the of the protein, is shown in SEQ ID NO:8. The amino acid sequence set forth in SEQ ID NO:8 was evaluated by BLASTP, yielding a pLog value of 113.00 versus the *Lycopersicon esculentum* sequence. A calculation of the percent similarity of the amino acid sequence set forth in SEQ ID NO:8 and the *Lycopersicon esculentum* sequence (using the Clustal algorithm) revealed that the protein encoded by SEQ ID NO: is 69% similar to the *Lycopersicon esculentum* IMP-3 protein.

FIG. 1 presents an alignment of the amino acid sequence set forth in SEQ ID NOs:2, 4, 6 and 8 with the *Lycopersicon esculentum* IMP amino acid sequences, SEQ ID NO:21 and 22. Alignments were performed using the Clustal algorithm.

These sequences represent the first rice, soybean and wheat sequences encoding myo-inositol-1 (or 4)-monophosphatase proteins.

Example 4

Characterization of cDNA Clones Encoding Extragenic Suppressor Proteins

The BLASTX search using the EST sequences from clones bsh1.pk0007. g11, cco1n.pk066. p15 and r10n.pk0062.c6 revealed similarity of the proteins encoded by the cDNAs to extragenic suppressor protein from *Synechocystis* sp. (NCBI Identification No. gi 3915048). The BLASTX search using the EST sequences from clones cdt2c.pk003.b20, s12.pk122.p24, src3c.pk013.g15, sfl1n.pk003. g19 and wlm0.pk0010.f6 revealed similarity of the proteins encoded by the cDNAs to extragenic suppressor protein from *Synechocystis* sp. (NCBI Identification No. gi 1652942).

In the process of comparing the ESTs it was found that soybean clones s12.pk122.p24, src3c.pk013.g15 and sfl1n.pk003.g19 had overlapping regions of homology. Using this homology it was possible to align the ESTs and assemble a contig encoding a unique soybean extragenic suppressor protein.

The BLAST results for each of the ESTs and the soybean contig are shown in Table 4:

TABLE 4

BLAST Results for Clones Encoding Polypeptides Homologous to *Synechocystis* sp Extragenic Suppressor Protein

| Clone | BLAST pLog Score |
|---|---|
| bsh1.pk0007.g11 | 46.10 |
| cco1n.pk066.p15 | 21.70 |
| cdt2c.pk003.b20 | 30.40 |
| rl0n.pk0062.c6 | 22.30 |
| Contig composed of clones:<br>sl2.pk122.p24<br>src3c.pk013.g15<br>sfl1n.pk003.g19 | 24.70 |
| wlm0.pk0010.f6 | 29.40 |

The sequence of a portion of the cDNA insert from clone bsh1.pk0007.g11 is shown in SEQ ID NO:9; the deduced amino acid sequence of this cDNA, which represents 74% of the of the protein (C-terminal region), is shown in SEQ ID NO:10. The amino acid sequence set forth in SEQ ID NO:10 was evaluated by BLASTP, yielding a pLog value of 40.30 versus the *Synechocystis* sp. sequence. A calculation of the percent similarity of the amino acid sequence set forth in SEQ ID NO:10 and the *Synechocystis* sp. sequence (using the Clustal algorithm) revealed that the protein encoded by SEQ ID NO:10 is 34% similar to the *Synechocystis* sp. extragenic suppressor protein.

The sequence of a portion of the cDNA insert from clone cco1n.pk066.p15 is shown in SEQ ID NO:11; the deduced amino acid sequence of this cDNA, which represents 40% of the of the protein (C-terminal region), is shown in SEQ ID NO:12. A calculation of the percent similarity of the amino acid sequence set forth in SEQ ID NO:12 and the *Synechocystis* sp. sequence (using the Clustal algorithm) revealed that the protein encoded by SEQ ID NO:12 is 34% similar to the *Synechocystis* sp. extragenic suppressor protein.

The sequence of the entire cDNA insert from clone cdt2c.pk003.b20 is shown in SEQ ID NO:13; the deduced amino acid sequence of this cDNA, which represents 100% of the of the protein, is shown in SEQ ID NO:14. The amino acid sequence set forth in SEQ ID NO:14 was evaluated by BLASTP, yielding a pLog value of 34.70 versus the *Synechocystis* sp. sequence. A calculation of the percent similarity of the amino acid sequence set forth in SEQ ID NO:14 and the *Synechocystis* sp. sequence (using the Clustal algorithm) revealed that the protein encoded by SEQ ID NO:14 is 28% similar to the *Synechocystis* sp. extragenic suppressor protein.

The sequence of a portion of the cDNA insert from clone r10n.pk0062.c6 is shown in SEQ ID NO:15; the deduced amino acid sequence of this cDNA, which represents 42% of the of the protein (C-terminal region), is shown in SEQ ID NO:16. The amino acid sequence set forth in SEQ ID NO:16 was evaluated by BLASTP, yielding a pLog value of 18.52 versus the *Synechocystis* sp. sequence. A calculation of the percent similarity of the amino acid sequence set forth in SEQ ID NO:16 and the *Synechocystis* sp. sequence (using the Clustal algorithm) revealed that the protein encoded by SEQ ID NO:16 is 33% similar to the *Synechocystis* sp. extragenic suppressor protein.

The sequence of the soybean contig composed of clones sl2. pk122.p24, src3c.pk013.g15 and sfl1n.pk003.g19 is shown in SEQ ID NO:17; the deduced amino acid sequence of this cDNA, which represents 100% of the of the protein, is shown in SEQ ID NO:18. The amino acid sequence set forth in SEQ ID NO:18 was evaluated by BLASTP, yielding a pLog value of 32.00 versus the *Synechocystis* sp. sequence. A calculation of the percent similarity of the amino acid sequence set forth in SEQ ID NO:18 and the *Synechocystis* sp. sequence (using the Clustal algorithm) revealed that the protein encoded by SEQ ID NO:18 is 26% similar to the *Synechocystis* sp. extragenic suppressor protein.

The sequence of a portion of the cDNA insert from clone wlm0.pk0010.f6 is shown in SEQ ID NO:19; the deduced amino acid sequence of this cDNA, which represents 96% of the of the protein, is shown in SEQ ID NO:20. The amino acid sequence set forth in SEQ ID NO:20 was evaluated by BLASTP, yielding a pLog value of 35.22 versus the *Synechocystis* sp. sequence. A calculation of the percent similarity of the amino acid sequence set forth in SEQ ID NO:20 and the *Synechocystis* sp. sequence (using the Clustal algorithm) revealed that the protein encoded by SEQ ID NO:20 is 25% similar to the *Synechocystis* sp. extragenic suppressor protein.

FIGS. 2A and 2B present an alignment of the amino acid sequence set forth in SEQ ID NOs:10, 12, 14, 16, 18 and 20 with the *Synechocystis* sp. extragenic suppressor protein amino acid sequences, SEQ ID NO:23 and 24. Alignments were performed using the Clustal algorithm.

These sequences represent the first plant sequences encoding extragenic suppressor proteins.

Example 5

Expression of Chimeric Genes in Monocot Cells

A chimeric gene comprising a cDNA encoding phytic acid biosynthetic enzyme in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML 103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalII fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding a phytic acid biosynthetic enzyme, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al., (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2.4-D. After two weeks the tissue can be transferred to regeneration medium (From et al., (1990) *Bio/Technology* 8:833–839).

Example 6

Expression of Chimeric Genes in Dicot Cells

A seed-specific expression cassette composed of the promoter and transcription terminator from the gene encoding the P subunit of the seed storage protein phaseolin from the bean *Phaseolus vulgaris* (Doyle et al. (1986) *J. Biol. Chem.* 261:9228–9238) can be used for expression of the instant phytic acid biosynthetic enzymes in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising a sequence encoding the phytic acid biosynthetic enzyme. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Kline et al. (1987) *Nature* (London) 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the phytic acid biosynthetic enzyme and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order):5 μL DNA (1 μg/μL), 20 μl spermidine (0.1 M), and 50 μL CaCl₂ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant phytic acid biosynthetic enzymes can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as decribed above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the phytic acid biosynthetic enzyme are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
   (a) a nucleotide sequence encoding a polypeptide having myo-inositol monophosphatase activity, wherein the polypeptide has an amino acid sequence of at least 90% sequence identity, based on the Clustal method of alignment, when compared to SEQ ID NO:8, or
   (b) a full-length complement of the nucleotide sequence of (a).

2. The polynucleotide of claim 1, wherein the amino acid sequence of the polypeptide has at least 95% sequence identity, based on the Clustal method of alignment, when compared to SEQ ID NO:8.

3. The polynucleotide of claim 1, wherein the amino acid sequence of the polypeptide comprises SEQ ID NO:8.

4. The polynucleotide of claim 1, wherein the nucleotide sequence comprises SEQ ID NO:7.

5. A vector comprising the polynucleotide of claim 1.

6. A recombinant DNA construct comprising the polynucleotide of claim 1 operably linked to suitable regulatory sequences.

7. A method for transforming a cell, comprising transforming a cell with the polynucleotide of claim 1.

8. A cell comprising the recombinant DNA construct of claim 6.

9. A method for producing a plant comprising transforming a plant cell with the polynucleotide of claim 1 and regenerating a plant from the transformed plant cell.

10. A plant comprising the recombinant DNA construct of claim 6.

11. A seed comprising the recombinant DNA construct of claim 6.

* * * * *

SEQUENCE LISTING

<160> NUMBER OF SEQ ID NOS: 24

<210> SEQ ID NO 1
<211> LENGTH: 462
<212> TYPE: DNA
<213> ORGANISM: Oryza sativa

<400> SEQUENCE: 1
cttacatgta agctcgtatt ttcttctcta cacaaccgaa aggtggagcg ttggcgaagg     60

```
accaaccaat tcctctctc taatcgccgc ggcgggggat agattgggag tgagcgcgta    120
tggcggagga gcagttcctc gccgtcgcgg tggacgccgc caagaacgcc ggcgagatca    180
tccgcaaggg cttctaccag accaagaacg tggagcacaa gggccaggtg gatttggtga    240
cggagacgga caaggcctgc gaggacctca tcttcaacca cctccggaag cactacccgg    300
accacaagtt catcggcgag gagacgtccg cggggctcgg cgccaccgcg gacctcaccg    360
acgacccgac ctggatcgtc gacccctcg atggcaccac caatttcgtc catggcttcc    420
cttttgtttg cgtctcgatc ggtctcaccg tcgggaaaat tc    462
```

<210> SEQ ID NO 2
<211> LENGTH: 114
<212> TYPE: PRT
<213> ORGANISM: Oryza sativa

<400> SEQUENCE: 2

```
Met Ala Glu Glu Gln Phe Leu Ala Val Ala Val Asp Ala Ala Lys Asn
 1               5                  10                  15

Ala Gly Glu Ile Ile Arg Lys Gly Phe Tyr Gln Thr Lys Asn Val Glu
            20                  25                  30

His Lys Gly Gln Val Asp Leu Val Thr Glu Thr Asp Lys Ala Cys Glu
        35                  40                  45

Asp Leu Ile Phe Asn His Leu Arg Lys His Tyr Pro Asp His Lys Phe
    50                  55                  60

Ile Gly Glu Glu Thr Ser Ala Gly Leu Gly Ala Thr Ala Asp Leu Thr
65                  70                  75                  80

Asp Asp Pro Thr Trp Ile Val Asp Pro Leu Asp Gly Thr Thr Asn Phe
                85                  90                  95

Val His Gly Phe Pro Phe Val Cys Val Ser Ile Gly Leu Thr Val Gly
            100                 105                 110

Lys Ile
    114
```

<210> SEQ ID NO 3
<211> LENGTH: 561
<212> TYPE: DNA
<213> ORGANISM: Glycine max
<220> FEATURE:
<221> NAME/KEY: unsure
<222> LOCATION: (529)..(530)
<223> OTHER INFORMATION: n = a, c, g or t
<220> FEATURE:
<221> NAME/KEY: unsure
<222> LOCATION: (543)
<223> OTHER INFORMATION: n = a, c, g or t
<220> FEATURE:
<221> NAME/KEY: unsure
<222> LOCATION: (546)
<223> OTHER INFORMATION: n = a, c, g or t
<220> FEATURE:
<221> NAME/KEY: unsure
<222> LOCATION: (552)
<223> OTHER INFORMATION: n = a, c, g or t
<220> FEATURE:
<221> NAME/KEY: unsure
<222> LOCATION: (556)
<223> OTHER INFORMATION: n = a, c, g or t

<400> SEQUENCE: 3

```
gaagaaagca gagcctctac tacatcatca cattcacatt tcagtacctt ctctttctcc    60
cagtctctca cacacaacaa ttgaagaaga aaatggttga caatgattcg ctctcggaat    120
```

```
tcctcgcatc tgcggtcgac gcggctcaga aagctggcga gattattcga aaaggcttct      180
accagaccaa aaatgtggaa cacaaaggac aggttgattt ggtcacagaa actgataaag      240
catgtgaaga actctatattt aatcatctga acagctttta tcccactcac aagttcattg     300
gggaagagac cacagctgcc tatggcacta cagaacttac agatgaaccc acatggatat     360
tgatccctgg atggaactac taacttgtgc atgggttccc tttgtttgtg tcccattggc     420
tcacaattgg aaaaatctac aattggtgtt gtatacaatc aatataatga cttttctgga     480
tcatggaaaa gtgccttttg atgggaatcc ataaatgtct cacaacgann atcagcctct     540
ctncantgag gngganaaaa c                                                561

<210> SEQ ID NO 4
<211> LENGTH: 168
<212> TYPE: PRT
<213> ORGANISM: Glycine max

<400> SEQUENCE: 4

Met Val Asp Asn Asp Ser Leu Ser Glu Phe Leu Ala Ser Ala Val Asp
  1               5                  10                  15

Ala Ala Gln Lys Ala Gly Glu Ile Ile Arg Lys Gly Phe Tyr Gln Thr
                 20                  25                  30

Lys Asn Val Glu His Lys Gly Gln Val Asp Leu Val Thr Glu Thr Asp
             35                  40                  45

Lys Ala Cys Glu Glu Leu Ile Phe Asn His Leu Lys Gln Leu Tyr Pro
         50                  55                  60

Thr His Lys Phe Ile Gly Glu Glu Thr Thr Ala Ala Tyr Gly Thr Thr
 65                  70                  75                  80

Glu Leu Thr Asp Glu Pro Thr Trp Ile Val Asp Pro Leu Asp Gly Thr
                 85                  90                  95

Thr Asn Phe Val His Gly Phe Pro Phe Val Cys Val Ser Ile Gly Leu
            100                 105                 110

Thr Ile Gly Lys Thr Pro Thr Ile Gly Val Val Tyr Asn Pro Ile Ile
        115                 120                 125

Asn Glu Leu Phe Thr Gly Ile His Gly Lys Gly Ala Phe Leu Asn Gly
    130                 135                 140

Asn Pro Ile Lys Val Ser Ser Gln Thr Glu Leu Ile Ser Ser Leu Leu
145                 150                 155                 160

Ala Thr Glu Ala Gly Thr Lys Arg
                165

<210> SEQ ID NO 5
<211> LENGTH: 667
<212> TYPE: DNA
<213> ORGANISM: Glycine max

<400> SEQUENCE: 5
gaattgcatg tggaaggctg gatgtattct ttgaacttgg ctttggtggt ccttgggatg      60
tagcaggtgg tgctgtcatt gttagagaag ctggaggtgt tgtatttgat ccgtccggtg     120
cagattttgc aataacatct cagcgagtag cagtttcaaa ccctttctaa aaggatgaac     180
ttgtggaaac tcggcgcaaa atgggtggg aaatttacaa ttaaccattg caagacctt      240 acaagatagc caacctttgt tagtccgtta acctttggcc caaagagttt tttagattcc     300
aagttttacg tagaagttcc aggttaaaaa ggttttagaa ttttaacttc ctccggggc      360 tcaagagaat ccataataaa tcaactttaa tcccttaac caagggccaa gtccaacgaa      420
```

```
aaaaaactcc ctaaacatgg gaagaagcac ctccacaggg cacgcgttcc caaacctggt    480
cggaaaggcc gtgggcattc gggaaaccgg taccaatcaa ggatcctccc ggaacccaaa    540
ggcaaggcaa accgcggcac gggcttgggc caaaccccgg tgaaccgccg cccaccaacg    600
gggagttcaa agcccaaggg gggaaaaggg gactttggcg gtccaaaact ttcacaaccg    660
ggggccg                                                             667
```

```
<210> SEQ ID NO 6
<211> LENGTH: 73
<212> TYPE: PRT
<213> ORGANISM: Glycine max
<220> FEATURE:
<221> NAME/KEY: UNSURE
<222> LOCATION: (56)
<223> OTHER INFORMATION: Xaa = any amino acid

<400> SEQUENCE: 6
```

Ile Ala Cys Gly Arg Leu Asp Val Phe Phe Glu Leu Gly Phe Gly Gly
 1               5                  10                  15

Pro Trp Asp Val Ala Gly Gly Ala Val Ile Val Arg Glu Ala Gly Gly
            20                  25                  30

Val Val Phe Asp Pro Ser Gly Ala Asp Phe Ala Ile Thr Ser Gln Arg
        35                  40                  45

Val Ala Val Ser Asn Pro Phe Xaa Lys Asp Glu Leu Val Glu Thr Arg
    50                  55                  60

Arg Lys Met Gly Trp Glu Ile Tyr Asn
 65                  70

```
<210> SEQ ID NO 7
<211> LENGTH: 1003
<212> TYPE: DNA
<213> ORGANISM: Triticum aestivum

<400> SEQUENCE: 7
acgagggaga ttcggaagcc atggcggagg agcagttcct ggccgcagct gtgggcgccg     60
ccaagagcgc cggcgagatt atccgcaaga gcttttacct aagcaagaaa gtggagcaca    120
agggccaggt ggatttggtg acggagacgg acaaggcatg cgaggatctc atcttcaacc    180
acctccggat gctctacccg gaccacaagt tcatcggcga ggagacgtct gcagccctcg    240
gctccaccga tgacctcacc tacgacccca cctggatagt cgacccccctc gatggcacca    300 ccaacttcgt tcatggcttt ccttttgtgt cgtctcgat tggcctcacc attgggaaga    360
ttcccaccgt tggagttgtg tacaacccca tcatgaatga gcttttcaca gctgttcgtg    420
gaaaaggtgc ttttctcaat ggctctccaa ttaaaacatc gcctcaaaat gagttggtga    480
aggctcttat ggtgacagag gtagggacca aaagagacaa gtccactttg gatgatacaa    540
ccaacagaat taataagtta ctattcaaga ttagatctat acgtatgtgt ggctcttttgg    600 ctctaaacat gtgtggagtt gcttgtggta ggctagattt gtgttatgag atcggttttg    660
gtggcccctg gatgtggct gctggagctt tgattctaaa ggaagctggg ggttttgttt    720
ttgatccgag cggtgatgag tttgatctga tggcgcaaag aatggcagga tcaaatggcc    780
acctcaagga tcagttcatc aaagcattgg gagatgcaag ctgaataact tatttctctt    840
ttcaagtaga atgaaagaat gtaagatggc cccaccaata agtaattgag ggctacttt    900 tgtgtagttc tatatgcata ttttgcaaac gtgcggatg taatgacatt ggatatattg    960
ctcgttttat ttaccatgca aggtgtgatc aaaaaaaaaa aaa                    1003
```

<210> SEQ ID NO 8
<211> LENGTH: 267
<212> TYPE: PRT
<213> ORGANISM: Triticum aestivum

<400> SEQUENCE: 8

```
Met Ala Glu Glu Gln Phe Leu Ala Ala Val Gly Ala Ala Lys Ser
  1               5                  10                  15
Ala Gly Glu Ile Ile Arg Lys Ser Phe Tyr Leu Ser Lys Lys Val Glu
             20                  25                  30
His Lys Gly Gln Val Asp Leu Val Thr Glu Thr Asp Lys Ala Cys Glu
         35                  40                  45
Asp Leu Ile Phe Asn His Leu Arg Met Leu Tyr Pro Asp His Lys Phe
     50                  55                  60
Ile Gly Glu Glu Thr Ser Ala Ala Leu Gly Ser Thr Asp Asp Leu Thr
 65                  70                  75                  80
Tyr Asp Pro Thr Trp Ile Val Asp Pro Leu Asp Gly Thr Thr Asn Phe
                 85                  90                  95
Val His Gly Phe Pro Phe Val Cys Val Ser Ile Gly Leu Thr Ile Gly
            100                 105                 110
Lys Ile Pro Thr Val Gly Val Val Tyr Asn Pro Ile Met Asn Glu Leu
        115                 120                 125
Phe Thr Ala Val Arg Gly Lys Gly Ala Phe Leu Asn Gly Ser Pro Ile
    130                 135                 140
Lys Thr Ser Pro Gln Asn Glu Leu Val Lys Ala Leu Met Val Thr Glu
145                 150                 155                 160
Val Gly Thr Lys Arg Asp Lys Ser Thr Leu Asp Asp Thr Thr Asn Arg
                165                 170                 175
Ile Asn Lys Leu Leu Phe Lys Ile Arg Ser Ile Arg Met Cys Gly Ser
            180                 185                 190
Leu Ala Leu Asn Met Cys Gly Val Ala Cys Gly Arg Leu Asp Leu Cys
        195                 200                 205
Tyr Glu Ile Gly Phe Gly Gly Pro Trp Asp Val Ala Ala Gly Ala Leu
    210                 215                 220
Ile Leu Lys Glu Ala Gly Gly Phe Val Phe Asp Pro Ser Gly Asp Glu
225                 230                 235                 240
Phe Asp Leu Met Ala Gln Arg Met Ala Gly Ser Asn Gly His Leu Lys
                245                 250                 255
Asp Gln Phe Ile Lys Ala Leu Gly Asp Ala Ser
            260                 265
```

<210> SEQ ID NO 9
<211> LENGTH: 1090
<212> TYPE: DNA
<213> ORGANISM: Hordeum vulgare

<400> SEQUENCE: 9

```
gcacgaggat aaactgagtg agtcagtcat tcttgaagtc gtgacgaaga acttcagaga    60
ccacctcata cttggggagg aaggtggcct tattggagat tctttgtcag agtatctctg   120
gtgcattgat cctttagatg gaacaacaaa cttgcacat ggttacccca gcttttctgt    180
atccattggt gttctttatc gaggcaagcc tgctgctgcc actgtggtgg aattttgtgg   240
tgggcctatg tgctggagca ctcgtacaat ttctgcatct tctggcaaag gtgcttattg   300
taatgggcaa aaaattcatg tcagtccaac agaaaaggtg gaacagtctc ttctggtaac   360
```

-continued

```
tgggtttgga tatgaacatg atgatgcatg gctcaccaat ataaatttgt tcaaggaatt      420
tactgatgtt agcagggag tacgaaggct aggctctgct gctgccgata tgtcccatgt       480
tggtctaggc attacagaag cctactggga atatcggctt aagccgtggg acatggctgc     540
tggcgttctg atagttgaag aagctggtgg agtagtgaca cgcatggatg gtggggagtt     600
tacagtcttt gatcgttctg ttcttgtttc caatggcgtt gttcatgatc agcttttgga     660
gcggatccgg cctgctactg aagatcttaa gaagaaagga attgatttct ccttgtggtt     720
taagcctgac aagtacccta ccgacttctg aatcacgctg ctcttcagct acttgttctc     780
tgtctagcaa aaataaggat gttttgctg aacaaccatg tacttagact gacaatacat      840
ttcaagaccc tttcactcaa ccggatcgaa aattaaagcc gaactttaca taaggagta      900
gagctcgaat gagcttctca ctggattcct tttgctttga tcgaatgtat caggaagaaa     960
tgtttgcaaa aggtgttgta tgcatggttc cagcctgttg tacttggaaa aatataactg    1020
ccaattttgt caatcatgga taatagcaag atctctcaag aagacatata ctaaaaaaaa    1080
aaaaaaaaaa                                                            1090
```

<210> SEQ ID NO 10
<211> LENGTH: 249
<212> TYPE: PRT
<213> ORGANISM: Hordeum vulgare

<400> SEQUENCE: 10

```
His Glu Asp Lys Leu Ser Glu Ser Val Ile Leu Glu Val Val Thr Lys
  1               5                  10                  15

Asn Phe Arg Asp His Leu Ile Leu Gly Glu Glu Gly Gly Leu Ile Gly
                 20                  25                  30

Asp Ser Leu Ser Glu Tyr Leu Trp Cys Ile Asp Pro Leu Asp Gly Thr
             35                  40                  45

Thr Asn Phe Ala His Gly Tyr Pro Ser Phe Ser Val Ser Ile Gly Val
         50                  55                  60

Leu Tyr Arg Gly Lys Pro Ala Ala Thr Val Val Glu Phe Cys Gly
 65                  70                  75                  80

Gly Pro Met Cys Trp Ser Thr Arg Thr Ile Ser Ala Ser Ser Gly Lys
                 85                  90                  95

Gly Ala Tyr Cys Asn Gly Gln Lys Ile His Val Ser Pro Thr Glu Lys
            100                 105                 110

Val Glu Gln Ser Leu Leu Val Thr Gly Phe Gly Tyr Glu His Asp Asp
        115                 120                 125

Ala Trp Leu Thr Asn Ile Asn Leu Phe Lys Glu Phe Thr Asp Val Ser
    130                 135                 140

Arg Gly Val Arg Arg Leu Gly Ser Ala Ala Ala Asp Met Ser His Val
145                 150                 155                 160

Gly Leu Gly Ile Thr Glu Ala Tyr Trp Glu Tyr Arg Leu Lys Pro Trp
                165                 170                 175

Asp Met Ala Ala Gly Val Leu Ile Val Glu Glu Ala Gly Val Val
            180                 185                 190

Thr Arg Met Asp Gly Gly Glu Phe Thr Val Phe Asp Arg Ser Val Leu
        195                 200                 205

Val Ser Asn Gly Val Val His Asp Gln Leu Leu Glu Arg Ile Arg Pro
    210                 215                 220

Ala Thr Glu Asp Leu Lys Lys Lys Gly Ile Asp Phe Ser Leu Trp Phe
225                 230                 235                 240
```

```
Lys Pro Asp Lys Tyr Pro Thr Asp Phe
                245
```

<210> SEQ ID NO 11
<211> LENGTH: 989
<212> TYPE: DNA
<213> ORGANISM: Zea mays

<400> SEQUENCE: 11

```
ttcaggagct tggctctctt gaaactcgag tcaaagaact gtacatcgta ttgccattac    60
aagtacagtg ctattgaact aaaaacatta ttgtttcttc ttgaaggacc ccccccccca   120
aaaaaaaatg atggctgctt tattatggtg gccaatggct ggtggtggtg cccttggtgc   180
agctcaaaag tcagtcgggt acttgtcagg cttgaaccac aacgagaagt cgatcccttt   240
cttcttaagg tcttcagtag gagggccgat ccggtccaaa agctgtccac acagacaaca   300
ctaagaacaa aacctgtcca tgaacgccac aaacaatatg ccaaattgtt cacaacaaac   360
aaacctgtcc atgaacaagt ccgttggaaa caagaacaga gcgatcgaag accgtaaact   420
ctccaccgtc catgcgagtt accacccac cagcttcctc tactatcagg acgccagcat   480
gcacatccca tggcttaagt cggtattccc agtaagcttc tgtaatacca agtccaatgt   540
gggacatgtc agcagcagca gacccgagcc ttcgcactcc cctgctaatg tcagtaaatt   600
ccttgaacag attcatattg gtcgtccagg catcatcgtg ttcatatcca aaacctgtga   660
cgagaagtga ttgttccacc ttgtctgtct gactgacatg aatcctttgt ccaatataat   720
aagctcctcc gccagcaaat ggaaaaattg ttcgggtggt ccaacacata aggccgccac   780
aaaattctca cccacttgaa accacacggg ttttcccagg aaagaacaac taatggcaca   840
ggtaaacccg ggggtaccat tggcaaagtt ccttgtctcc accaaggggt aattgcccca   900
aaggtctcct gaaagggaat ctccaaaaag ggcgcctttt ccccccaatt aaggggggc    960
ttttaattct ttggggaaaa tctcaaaag                                     989
```

<210> SEQ ID NO 12
<211> LENGTH: 136
<212> TYPE: PRT
<213> ORGANISM: Zea mays

<400> SEQUENCE: 12

```
Met Cys Trp Thr Thr Arg Thr Ile Phe Pro Phe Ala Gly Gly Gly Ala
  1               5                  10                  15

Tyr Tyr Ile Gly Gln Arg Ile His Val Ser Gln Thr Asp Lys Val Glu
             20                  25                  30

Gln Ser Leu Leu Val Thr Gly Phe Gly Tyr Glu His Asp Asp Ala Trp
         35                  40                  45

Thr Thr Asn Met Asn Leu Phe Lys Glu Phe Thr Asp Ile Ser Arg Gly
     50                  55                  60

Val Arg Arg Leu Gly Ser Ala Ala Asp Met Ser His Ile Gly Leu
 65                  70                  75                  80

Gly Ile Thr Glu Ala Tyr Trp Glu Tyr Arg Leu Lys Pro Trp Asp Val
                 85                  90                  95

His Ala Gly Val Leu Ile Val Glu Glu Ala Gly Gly Val Val Thr Arg
            100                 105                 110

Met Asp Gly Gly Glu Phe Thr Val Phe Asp Arg Ser Val Leu Val Ser
        115                 120                 125

Asn Gly Leu Val His Gly Gln Val
    130                 135
```

-continued

<210> SEQ ID NO 13
<211> LENGTH: 492
<212> TYPE: DNA
<213> ORGANISM: Zea mays
<220> FEATURE:
<221> NAME/KEY: unsure
<222> LOCATION: (351)
<223> OTHER INFORMATION: n = a, c, g or t
<220> FEATURE:
<221> NAME/KEY: unsure
<222> LOCATION: (442)
<223> OTHER INFORMATION: n = a, c, g or t
<220> FEATURE:
<221> NAME/KEY: unsure
<222> LOCATION: (485)
<223> OTHER INFORMATION: n = a, c, g or t

<400> SEQUENCE: 13

```
agctccgagc gtcattctcc gccccgacat ttaaaccttg ctcccgacaa ccgccgccga    60
ctcctcccca atgctctcct cttcctcctc cacccactcg gccacctcgc ccttccccgg   120
cctcgcctcc gcaaacccta accccgctc tcgcctcctc cgcctccgcg ccgcctcgcc    180
cgtgtcgtcc gcggtcttga gcgcgagtgg gcgccagccg atgagtacgg ttagggcctc   240
gttcgccgct ggggcggccg gccggagagc tgcggcagtg ggggagttgg cgacggagcg   300
gctggtggag gtggcgcaac gggcggcgga cgctgctggg gaggtgctca ngaagtactt   360
ccgccagcgg gttgagatca tcgacaaaga ggaccacagt cctgttacaa ttgcagatag   420
aagaagcaga agaagcaatg gngtcagtta tactgaagag cttccctact caagccaatt   480
ttgggnaaga ga                                                       492
```

<210> SEQ ID NO 14
<211> LENGTH: 338
<212> TYPE: PRT
<213> ORGANISM: Zea mays

<400> SEQUENCE: 14

```
Met Leu Ser Ser Ser Ser Thr His Ser Asp Thr Ser Pro Phe Pro
 1               5                  10                  15

Gly Leu Ala Ser Ala Asn Pro Asn Pro Arg Ser Arg Leu Leu Arg Leu
             20                  25                  30

Arg Ala Ala Ser Pro Val Ser Ser Ala Val Leu Ser Ala Ser Gly Arg
         35                  40                  45

Gln Pro Met Ser Thr Val Arg Ala Ser Phe Ala Ala Gly Ala Ala Gly
     50                  55                  60

Arg Arg Ala Ala Ala Val Gly Glu Leu Ala Thr Glu Arg Leu Val Glu
 65                  70                  75                  80

Val Ala Gln Arg Ala Ala Asp Ala Ala Gly Glu Val Leu Arg Lys Tyr
                 85                  90                  95

Phe Arg Gln Arg Val Glu Ile Ile Asp Lys Glu Asp His Ser Pro Val
            100                 105                 110

Thr Ile Ala Asp Arg Glu Ala Glu Glu Ala Met Val Ser Val Ile Leu
        115                 120                 125

Lys Ser Phe Pro Thr His Ala Ile Phe Gly Glu Glu Asn Gly Trp Arg
    130                 135                 140

Cys Ala Glu Asn Ser Ala Asp Phe Val Trp Val Leu Asp Pro Ile Asp
145                 150                 155                 160

Gly Thr Lys Ser Phe Ile Thr Gly Lys Pro Leu Phe Gly Thr Leu Ile
                165                 170                 175
```

Ala Leu Leu His Asn Gly Lys Pro Val Ile Gly Val Ile Asp Gln Pro
            180                 185                 190

Ile Leu Arg Glu Arg Trp Ile Gly Val Asp Gly Lys Gln Thr Thr Leu
        195                 200                 205

Asn Gly Gln Glu Ile Ser Val Arg Ser Cys Asn Leu Leu Ala Gln Ala
    210                 215                 220

Tyr Leu Tyr Thr Thr Ser Pro His Leu Phe Glu Ala Asp Ala Glu Asp
225                 230                 235                 240

Ala Phe Ile Arg Val Arg Asn Lys Val Lys Val Pro Leu Tyr Gly Cys
                245                 250                 255

Asp Cys Tyr Ala Tyr Ala Leu Leu Ala Ser Gly Phe Val Asp Ile Val
            260                 265                 270

Val Glu Ser Gly Leu Lys Pro Tyr Asp Phe Leu Ser Leu Val Pro Val
        275                 280                 285

Ile Glu Gly Ala Gly Gly Ser Ile Thr Asp Trp Arg Gly Asp Lys Leu
    290                 295                 300

His Trp Pro Val Thr Ala Glu Ser Arg Pro Thr Ser Phe Asn Val Val
305                 310                 315                 320

Ala Ala Gly Asp Ala Arg Val His Lys Glu Ala Leu Asp Ala Leu Arg
                325                 330                 335

Trp Arg

<210> SEQ ID NO 15
<211> LENGTH: 593
<212> TYPE: DNA
<213> ORGANISM: Oryza sativa

<400> SEQUENCE: 15
gcacgagctt acaaaggtgg aacaatcact tctggtaact ggttttggtt atgaacatga      60
tgatgcatgg gtgaccaaca taaatttgtt caaggaatac acagacatta gcaggggagt     120
acgaagacta ggttctgctg ctgctgacat gtcccacgtt gccctaggca ttacagaagc     180
ctactgggaa taccgactta agccttggga tatggctgct ggtgttctga tagttgaaga     240
agctggtggg atggtgtcac gcatggatgg tggggagttt accgtctttg atcgttctgt     300
ccttgtttcc aatggtgttg tacatgatca gcttttggat cggattggcc ctgccacaga     360
agatcttaag aagaaaggaa ttgatttctc cttgtggttt aaacccgaca ataccctac     420 cgactttta gttgaactcc tcacccagag ctattttata ctactagaag aaaagagaaa     480
aacagaggat cttatgttaa atgccatgt acttgactga atatttgttt attgaagtcc     540
tttgactcaa aaaaaaaaaa aaaaaaaaac tcgagggggg gccggtacac aat           593

<210> SEQ ID NO 16
<211> LENGTH: 142
<212> TYPE: PRT
<213> ORGANISM: Oryza sativa

<400> SEQUENCE: 16

His Glu Leu Thr Lys Val Glu Gln Ser Leu Val Thr Gly Phe Gly
 1               5                  10                  15

Tyr Glu His Asp Asp Ala Trp Val Thr Asn Ile Asn Leu Phe Lys Glu
                20                  25                  30

Tyr Thr Asp Ile Ser Arg Gly Val Arg Arg Leu Gly Ser Ala Ala Ala
            35                  40                  45

Asp Met Ser His Val Ala Leu Gly Ile Thr Glu Ala Tyr Trp Glu Tyr

```
                50              55              60
Arg Leu Lys Pro Trp Asp Met Ala Ala Gly Val Leu Ile Val Glu Glu
 65                  70                  75                  80

Ala Gly Gly Met Val Ser Arg Met Asp Gly Gly Glu Phe Thr Val Phe
                 85                  90                  95

Asp Arg Ser Val Leu Val Ser Asn Gly Val Val His Asp Gln Leu Leu
            100                 105                 110

Asp Arg Ile Gly Pro Ala Thr Glu Asp Leu Lys Lys Gly Ile Asp
        115                 120                 125

Phe Ser Leu Trp Phe Lys Pro Asp Lys Tyr Pro Thr Asp Phe
130                 135                 140
```

<210> SEQ ID NO 17
<211> LENGTH: 1103
<212> TYPE: DNA
<213> ORGANISM: Glycine max

<400> SEQUENCE: 17

```
caattgcaat gttctcacag tgccattttc tctctcactc cccaattccc aatactacct      60
ttcgtctcag agccatggcg cctcacagca cgcctcttga actcaatcgc ttcgccgagg     120
tcggtaacaa agtcgccgat gctgccggag aagttatccg caaatacttc agaaaaaact     180
tcgacgttat tcacaaacat gatctcagtc cagtaaccat gcagatcaa tctgctgagg      240
aggctatggt ttcaatcata ctagacaatt tcccttctca tgccatttac ggagaggaaa     300
atgggtggag gtgtgaagaa agaatgctga ttatgtttg ggtattagat cccatagatg      360
ggactaagag ctttattact gggaaacctg tatttggtac tctcgttgct cttctacaaa     420
atggcacacc aatccttggc ataattgatc aacctgtgtt aagagaaagg tggatcggga     480
tagcaggaaa gagaacctca ctgaacggac aagaaatatc tacacgcact tgtgcggacc     540
tttctcaagc atacctgtac accacaagcc cacatctgtt caatggagat gcagaagaag     600
cattcattcg tgttagaagc aaggtaaaat tccaattgta tggctgcgac tgctatgcat     660
atgcactttt gtcttctggt tttgtggatc ttgttgttga gtctggtctg aagccatacg     720
attttcttgc attgattcct gttattgaag gcgctggagg tgtcataact gattggaaag     780
gagataaact gttttgggaa gcttctccac tttcaatcgc cacaagtttt aatgttgtgg     840
ctgctggtga caaacagatt catcaacaag ctctagattc attgcagtgg aagtgatagc     900
ttgaattaat cttcagtgca ataatcttc tctgcaaatg gtcttgattc agatgttcct     960
aaggacatgt attaccgtac cattttctgg catttaagtt gaaaaccatg tactcagaat    1020
cttgaataag ttcctgcaga aattaacctc tttgtctatt ggttggtaaa aaaggggggg    1080
gccgtacaaa tctccccgcc ccg                                            1103
```

<210> SEQ ID NO 18
<211> LENGTH: 295
<212> TYPE: PRT
<213> ORGANISM: Glycine max

<400> SEQUENCE: 18

```
Met Phe Ser Gln Cys His Phe Leu Ser His Ser Pro Ile Pro Asn Thr
  1               5                  10                  15

Thr Phe Arg Leu Arg Ala Met Ala Pro His Ser Thr Pro Leu Glu Leu
             20                  25                  30

Asn Arg Phe Ala Glu Val Gly Asn Lys Val Ala Asp Ala Ala Gly Glu
         35                  40                  45
```

Val Ile Arg Lys Tyr Phe Arg Lys Asn Phe Asp Val Ile His Lys His
 50                  55                  60

Asp Leu Ser Pro Val Thr Ile Ala Asp Gln Ser Ala Glu Glu Ala Met
 65                  70                  75                  80

Val Ser Ile Ile Leu Asp Asn Phe Pro Ser His Ala Ile Tyr Gly Glu
                 85                  90                  95

Glu Asn Gly Trp Arg Cys Glu Glu Lys Asn Ala Asp Tyr Val Trp Val
                100                 105                 110

Leu Asp Pro Ile Asp Gly Thr Lys Ser Phe Ile Thr Gly Lys Pro Val
            115                 120                 125

Phe Gly Thr Leu Val Ala Leu Leu Gln Asn Gly Thr Pro Ile Leu Gly
130                 135                 140

Ile Ile Asp Gln Pro Val Leu Arg Glu Arg Trp Ile Gly Ile Ala Gly
145                 150                 155                 160

Lys Arg Thr Ser Leu Asn Gly Gln Glu Ile Ser Thr Arg Thr Cys Ala
                165                 170                 175

Asp Leu Ser Gln Ala Tyr Leu Tyr Thr Thr Ser Pro His Leu Phe Asn
            180                 185                 190

Gly Asp Ala Glu Glu Ala Phe Ile Arg Val Arg Ser Lys Val Lys Phe
        195                 200                 205

Gln Leu Tyr Gly Cys Asp Cys Tyr Ala Tyr Ala Leu Leu Ser Ser Gly
210                 215                 220

Phe Val Asp Leu Val Val Glu Ser Gly Leu Lys Pro Tyr Asp Phe Leu
225                 230                 235                 240

Ala Leu Ile Pro Val Ile Glu Gly Ala Gly Gly Val Ile Thr Asp Trp
                245                 250                 255

Lys Gly Asp Lys Leu Phe Trp Glu Ala Ser Pro Leu Ser Ile Ala Thr
            260                 265                 270

Ser Phe Asn Val Val Ala Ala Gly Asp Lys Gln Ile His Gln Gln Ala
        275                 280                 285

Leu Asp Ser Leu Gln Trp Lys
290                 295

<210> SEQ ID NO 19
<211> LENGTH: 1418
<212> TYPE: DNA
<213> ORGANISM: Triticum aestivum

<400> SEQUENCE: 19
gcacgagaca aaacctagcc tcccttacca cctccgctcg ccctccctcc tgcaacctt      60 ctcctcctcc gcggcgggtc gggcctgcgg gatagcgggc cgttggatgg gctcggttcg    120
agcctcgccc tctgaggcgg ggggctgggc ggtggctgcg gcgggtaagg aggggggtgga  180 catggagcgg ctggtggcgg tggcgcagag cgcggcggat gcggcggggg aggtgctcag    240
gaagtacttc aggcagcgct cgagatcat cgacaaagag gaccacagtc ccgtcacgat    300
cgctgataga gaagcagaag aagcaatgac ctcagtcata ctgaagagct ttcctactca    360
tgctgttttc ggtgaggaga acggttggag gtgtgcagag aagtctgctg actatgtttg    420
ggtcttggac cccatagatg gaacaaagag cttcataact gggaagcctc tttttggtac    480
gcttattgcg cttcttcaca atggaaagcc ggttatgggc attattgatc agccaatctt    540
gagagagaga tgggttgggg tgacgggaa gaaaactacc ttaaatggac aagaaatatc    600
tgtccgtcct tgcaatgtac tggagcaagc ttacttatat actacgagtc cacatctctt    660

-continued

```
tgaaggagat gctgaagatg cattcattcg tgtacgagac aaggtgaaag tcccattgta      720
tggctgtgat tgttatgctt atgctctcct ggcttctggt tttgtggatc ttgttgttga      780
atctggattg aagccatacg attttctctc gctggtaccg gtgattgaag gagctggggg      840
ctcaataact gattgggaag ggaacaagct ccactggcct gtctcttcgg aatctcggcc      900
aacaagtttc aacgtggtgg cagccggaga tttcccatgtc catgggcagg ccctggcagc      960
gttgcggtgg cgctagcctg cctgcagcac ggggcggctc ctattgttca tttagaaggc     1020
tgcaactgtt attcatctat ccaataaaac tgagtctgta cgcttcctca gtgggtaaag     1080
caagttgttc acggtgcacc ctttactcaa taatgatcag tggtttcttg ttgtgtgtta     1140
aaaaaaaaaa aaaaaaaaaa aaaaaaaaaa aaaaaaaaaa aaaaaaaaaa aaaaaaaaaa     1200
aaaaaaaaaa aaaaacaaa aaaaaaaata aaaaaaaaaa aaaccccccg ggggggggc     1260 ggggaccaaa tttcccccata tttttttttt ttttaccccc ccccaggggg gttttttttta   1320 taaaacttct gagggggaa aaaccggggg tttaaccaaa taaatcccct tgaacaaaaa      1380
cccccttccc ccaaggggg taataaaaaaa aagggccg                             1418
```

```
<210> SEQ ID NO 20
<211> LENGTH: 324
<212> TYPE: PRT
<213> ORGANISM: Triticum aestivum

<400> SEQUENCE: 20
```

```
His Glu Thr Lys Pro Ser Leu Pro Tyr His Leu Arg Ser Pro Ser Leu
  1               5                  10                  15

Leu Ala Thr Phe Ser Ser Ala Ala Gly Arg Ala Cys Gly Ile Ala
             20                  25                  30

Gly Arg Trp Met Gly Ser Val Arg Ala Ser Pro Ser Glu Ala Gly Gly
         35                  40                  45

Trp Ala Val Ala Ala Gly Lys Glu Gly Val Asp Met Glu Arg Leu
     50                  55                  60

Val Ala Val Ala Gln Ser Ala Ala Asp Ala Ala Gly Glu Val Leu Arg
 65                  70                  75                  80

Lys Tyr Phe Arg Gln Arg Phe Glu Ile Ile Asp Lys Glu Asp His Ser
                 85                  90                  95

Pro Val Thr Ile Ala Asp Arg Glu Ala Glu Glu Ala Met Thr Ser Val
            100                 105                 110

Ile Leu Lys Ser Phe Pro Thr His Ala Val Phe Gly Glu Glu Asn Gly
        115                 120                 125

Trp Arg Cys Ala Glu Lys Ser Ala Asp Tyr Val Trp Val Leu Asp Pro
    130                 135                 140

Ile Asp Gly Thr Lys Ser Phe Ile Thr Gly Lys Pro Leu Phe Gly Thr
145                 150                 155                 160

Leu Ile Ala Leu Leu His Asn Gly Lys Pro Val Met Gly Ile Ile Asp
                165                 170                 175

Gln Pro Ile Leu Arg Glu Arg Trp Val Gly Val Asp Gly Lys Lys Thr
            180                 185                 190

Thr Leu Asn Gly Gln Glu Ile Ser Val Arg Pro Cys Asn Val Leu Glu
        195                 200                 205

Gln Ala Tyr Leu Tyr Thr Thr Ser Pro His Leu Phe Glu Gly Asp Ala
    210                 215                 220

Glu Asp Ala Phe Ile Arg Val Arg Asp Lys Val Lys Val Pro Leu Tyr
225                 230                 235                 240
```

```
Gly Cys Asp Cys Tyr Ala Tyr Ala Leu Leu Ala Ser Gly Phe Val Asp
                245                 250                 255

Leu Val Val Glu Ser Gly Leu Lys Pro Tyr Asp Phe Leu Ser Leu Val
            260                 265                 270

Pro Val Ile Glu Gly Ala Gly Ser Ile Thr Asp Trp Glu Gly Asn
        275                 280                 285

Lys Leu His Trp Pro Val Ser Ser Glu Ser Arg Pro Thr Ser Phe Asn
    290                 295                 300

Val Val Ala Ala Gly Asp Ser His Val His Gly Gln Ala Leu Ala Ala
305                 310                 315                 320

Leu Arg Trp Arg

<210> SEQ ID NO 21
<211> LENGTH: 273
<212> TYPE: PRT
<213> ORGANISM: Lycopersicon esculentum

<400> SEQUENCE: 21

Met Ala Arg Asn Gly Ser Leu Glu Glu Phe Leu Gly Val Ala Val Asp
1               5                   10                  15

Ala Ala Lys Arg Ala Gly Glu Ile Ile Arg Lys Gly Phe His Glu Thr
            20                  25                  30

Lys His Val Val His Lys Gly Gln Val Asp Leu Val Thr Glu Thr Asp
        35                  40                  45

Lys Ala Cys Glu Asp Leu Ile Phe Asn His Leu Lys Gln His Phe Pro
    50                  55                  60

Ser His Lys Phe Ile Gly Glu Thr Ser Ala Ala Thr Gly Asp Phe
65                  70                  75                  80

Asp Leu Thr Asp Glu Pro Thr Trp Ile Val Asp Pro Val Asp Gly Thr
                85                  90                  95

Thr Asn Phe Val His Gly Phe Pro Ser Val Cys Val Ser Ile Gly Leu
            100                 105                 110

Thr Ile Gly Lys Ile Pro Thr Val Gly Val Val Tyr Asp Pro Ile Ile
        115                 120                 125

Asp Glu Leu Phe Thr Gly Ile Asn Gly Lys Gly Ala Tyr Leu Asn Gly
    130                 135                 140

Lys Pro Ile Lys Val Ser Ser Gln Ser Glu Leu Val Lys Ser Leu Leu
145                 150                 155                 160

Gly Thr Glu Val Gly Thr Thr Arg Asp Asn Leu Thr Val Glu Thr Thr
                165                 170                 175

Thr Arg Arg Ile Asn Asn Leu Leu Phe Lys Val Arg Ser Leu Arg Met
            180                 185                 190

Cys Gly Ser Cys Ala Leu Asp Leu Cys Trp Val Ala Cys Gly Arg Leu
        195                 200                 205

Glu Leu Phe Tyr Leu Ile Gly Tyr Gly Gly Pro Trp Asp Val Ala Gly
    210                 215                 220

Gly Ala Val Ile Val Lys Glu Ala Gly Gly Val Leu Phe Asp Pro Ser
225                 230                 235                 240

Gly Ser Glu Phe Asp Ile Thr Ser Gln Arg Val Ala Ala Thr Asn Pro
                245                 250                 255

His Leu Lys Glu Ala Phe Val Glu Ala Leu Gln Leu Ser Glu Tyr Val
            260                 265                 270

Ser
```

```
<210> SEQ ID NO 22
<211> LENGTH: 268
<212> TYPE: PRT
<213> ORGANISM: Lycopersicon esculentum

<400> SEQUENCE: 22

Met Ala Gln Asn Gly Ser Val Glu Gln Phe Leu Asp Val Ala Val Glu
  1               5                  10                  15

Ala Ala Lys Lys Ala Gly Glu Ile Ile Arg Glu Gly Phe Tyr Lys Thr
             20                  25                  30

Lys His Val Glu His Lys Gly Met Val Asp Leu Val Thr Glu Thr Asp
         35                  40                  45

Lys Ala Cys Glu Asp Phe Ile Phe Asn His Leu Lys Gln Arg Phe Pro
     50                  55                  60

Ser His Lys Phe Ile Gly Glu Glu Thr Thr Ala Ala Cys Gly Asn Phe
 65                  70                  75                  80

Glu Leu Thr Asp Glu Pro Thr Trp Ile Val Asp Pro Leu Asp Gly Thr
                 85                  90                  95

Thr Asn Phe Val His Gly Phe Pro Phe Val Cys Val Ser Ile Gly Leu
            100                 105                 110

Thr Ile Glu Lys Lys Pro Thr Val Gly Val Val Tyr Asn Pro Ile Ile
        115                 120                 125

Asp Glu Leu Phe Thr Gly Ile Asp Gly Lys Gly Ala Phe Leu Asn Gly
    130                 135                 140

Lys Pro Ile Lys Val Ser Ser Gln Ser Glu Leu Val Lys Ala Leu Leu
145                 150                 155                 160

Ala Thr Glu Ala Gly Thr Asn Arg Asp Lys Leu Val Val Asp Ala Thr
                165                 170                 175

Thr Gly Arg Ile Asn Ser Leu Leu Phe Lys Val Arg Ser Leu Arg Met
            180                 185                 190

Cys Gly Ser Cys Ala Leu Asn Leu Cys Gly Val Ala Cys Gly Arg Leu
        195                 200                 205

Asp Leu Phe Tyr Glu Leu Glu Phe Gly Gly Pro Trp Asp Val Ala Gly
    210                 215                 220

Gly Ala Val Ile Val Lys Glu Ala Gly Gly Phe Val Phe Asp Pro Ser
225                 230                 235                 240

Gly Ser Glu Phe Asp Leu Thr Ala Arg Arg Val Ala Ala Thr Asn Ala
                245                 250                 255

His Leu Lys Asp Ala Phe Ile Lys Ala Leu Asn Glu
            260                 265

<210> SEQ ID NO 23
<211> LENGTH: 287
<212> TYPE: PRT
<213> ORGANISM: Synechocystis sp.

<400> SEQUENCE: 23

Met Thr Ser Ala Gln Lys Pro Val Phe Ser Pro Ser Asp Leu Gln Thr
  1               5                  10                  15

Trp Leu Glu Ile Ala Thr Glu Ala Val Leu Ala Ala Gly Ala Glu Ile
             20                  25                  30

Phe Ser Leu Trp Gly Lys Val Gln Gln Ile Gln Glu Lys Gly Arg Ala
         35                  40                  45

Gly Asp Leu Val Thr Glu Ala Asp Arg Gln Ala Glu Ala Ile Ile Leu
     50                  55                  60

Glu Ile Ile Lys Arg Arg Cys Pro Asp His Ala Ile Leu Ala Glu Glu
```

```
              65                  70                  75                  80
Ser Gly Gln Leu Gly Gln Val Asp Asn Pro Phe Cys Trp Ala Ile Asp
                    85                  90                  95

Pro Leu Asp Gly Thr Thr Asn Phe Ala His Ser Tyr Pro Val Ser Cys
                100                 105                 110

Val Ser Ile Gly Leu Leu Ile Gln Asp Ile Pro Thr Val Gly Val Val
                115                 120                 125

Tyr Asn Pro Phe Arg Gln Glu Leu Phe Arg Ala Ala Thr Ser Leu Gly
            130                 135                 140

Ala Thr Leu Asn Arg Arg Pro Ile Gln Val Ser Thr Ala Ser Leu
145                 150                 155                 160

Asp Lys Ser Leu Leu Val Thr Gly Phe Ala Tyr Asp Arg Val Lys Thr
                165                 170                 175

Leu Asp Asn Asn Tyr Pro Glu Phe Cys Tyr Leu Thr His Leu Thr Gln
                180                 185                 190

Gly Val Arg Arg Ser Gly Ser Ala Ala Ile Asp Leu Ile Asp Val Ala
                195                 200                 205

Cys Gly Arg Leu Asp Gly Tyr Trp Glu Arg Gly Ile Asn Pro Trp Asp
            210                 215                 220

Met Ala Ala Gly Ile Val Ile Val Arg Glu Ala Gly Gly Ile Val Ser
225                 230                 235                 240

Ala Tyr Asp Cys Ser Pro Leu Asp Leu Ser Thr Gly Arg Ile Leu Ala
                245                 250                 255

Thr Asn Gly Lys Ile His Gln Glu Leu Ser Gln Ala Leu Ala Ala Thr
            260                 265                 270

Pro Gln Trp Phe Gln Tyr Ala Ala Ala Arg Ala Gln Lys Ile
            275                 280                 285

<210> SEQ ID NO 24
<211> LENGTH: 267
<212> TYPE: PRT
<213> ORGANISM: Synechocystis sp.

<400> SEQUENCE: 24

Met Leu Pro Glu Val Glu Gln Arg Leu Phe Ile Ala Gln Gln Leu Ala
  1               5                  10                  15

Ala Val Ser Gly Glu Ile Leu Ile Gln Tyr Phe Arg Arg Ser His Leu
                 20                  25                  30

Gln Gly Gly Thr Lys Ile Asp Gln Val Ser Ala Ile Val Thr Gln Ala
            35                  40                  45

Asp Glu Glu Ala Glu Gln Ala Met Val Asp Leu Ile Gln Ala Gln Phe
 50                  55                  60

Pro Gln Asp Gly Val Ile Arg Glu Glu Gly Lys Asn Ile Ala Gly Lys
 65                  70                  75                  80

Ser Gly Tyr Thr Trp Val Leu Asp Pro Ile Asp Gly Thr Ser Ser Phe
                 85                  90                  95

Val Arg Gly Leu Pro Ile Phe Ala Thr Leu Ile Gly Leu Val Asp Ala
                100                 105                 110

Asp Met Arg Pro Val Leu Gly Ile Ala His Gln Pro Ile Ser Gly Asp
            115                 120                 125

Arg Trp Gln Gly Val Gln Gly Glu Gln Ser Asn Val Asn Gly Ile Pro
        130                 135                 140

Leu Val Asn Pro Tyr Lys Ala Ser Glu Ile Asn Leu Thr Ala Ala Cys
145                 150                 155                 160
```

```
Ile Val Ser Thr Thr Pro Leu Met Phe Thr Thr Pro Val Gln Gln Gln
            165             170             175

Lys Met Ala Asp Ile Tyr Arg Gln Cys Gln Arg Thr Ala Phe Gly Gly
            180             185             190

Asp Cys Phe Asn Tyr Leu Ser Ala Ala Ser Gly Trp Thr Ala Met Pro
        195             200             205

Leu Val Ile Val Glu Ala Asp Leu Asn Phe Tyr Asp Phe Cys Ala Leu
    210             215             220

Ile Pro Ile Leu Thr Gly Ala Asn Tyr Cys Phe Thr Asp Trp Gln Gly
225             230             235             240

Lys Glu Leu Thr Pro Glu Ser Thr Glu Val Val Ala Ser Pro Asn Pro
            245             250             255

Lys Leu His Ser Glu Ile Leu Ala Phe Leu Gln
            260             265
```